United States Patent [19]

Knapp

[11] Patent Number: 5,250,717
[45] Date of Patent: Oct. 5, 1993

[54] PROCESS FOR PREPARING N,N-DIARYLTHIOUREAS AND ARYLISOTHIOCYANATES

[75] Inventor: Gordon G. Knapp, Baton Rouge, La.

[73] Assignee: Ethyl Corporation, Richmond, Va.

[21] Appl. No.: 891,250

[22] Filed: Jun. 1, 1992

Related U.S. Application Data

[62] Division of Ser. No. 601,238, Oct. 22, 1990, abandoned.

[51] Int. Cl.$^5$ .................. C07C 209/60; C07C 335/20
[52] U.S. Cl. ........................................ 558/18; 564/27
[58] Field of Search ............................ 558/18; 564/27

[56] References Cited

U.S. PATENT DOCUMENTS

| | | | |
|---|---|---|---|
| 3,530,161 | 9/1970 | Hull | 260/454 |
| 4,234,513 | 11/1980 | Papenfuhs | 564/27 |

OTHER PUBLICATIONS

CA:51:18700d (1957).
CA 60:2825g (1964).
CA 60:4059g (1964).

*Primary Examiner*—Joseph Paul Brust
*Assistant Examiner*—Jacqueline Haley
*Attorney, Agent, or Firm*—Richard J. Hammond

[57] ABSTRACT

Isothiocyanates of the formula

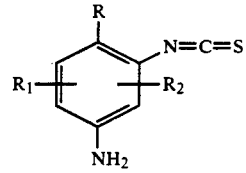

where R, $R_1$, and $R_2$ are the same or different and are hydrogen or $C_1$ to $C_6$ linear or branched alkyl and thioureas of the formula

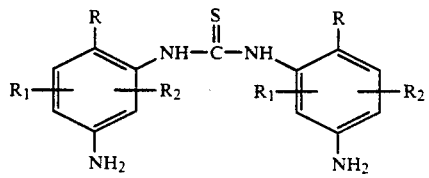

where R, $R_1$, and $R_2$ are defined above, are disclosed. Processes for their preparation are also disclosed.

8 Claims, No Drawings

PROCESS FOR PREPARING N,N-DIARYLTHIOUREAS AND ARYLISOTHIOCYANATES

This application is a division of application Ser. No. 07/601,238, filed Oct. 22, 1990, now abandoned.

FIELD OF THE INVENTION

This invention relates to a process for preparing N,N'-diarylthioureas. More particularly, this invention relates to thiourea reactions with aromatic amines and to N,N'-diarylthioureas and arylisothiocyanates prepared from such reactions.

BACKGROUND

The preparation and use of organic isocyanates and ureas are closely parrelled by the analogous organo isothiocyanates and thioureas.

One of the most commonly and easily effected preparative routes to organo isothiocyanates is the thiophosgenation route where a salt of a primary amine (for example, in a slurry with toluene as the slurry agent) is reacted with thiophosgene. See, for example, U. K. Patent No. 779,806.

In German Patent No. 1,148,540, a metathesis reaction is carried out by treating substituted benzyl halides having at least one hydrogen on the halide carbon with potassium thiocyanate. An iodide or bromide catalyst is used to promote the reaction which is carried out in an inert solvent such as dimethylsulfoxide.

In a process somewhat similar to the above described thiophosgenation reaction, U.S. Pat. No. 3,530,161 discloses the reaction of an aromatic nitro compound with carbon monoxide and carbon disulfide in the presence of a catalytic amount of iron (II) or cobalt (IV) carbonyl. The preparation of aromatic isothiocyanates from such reaction is particularly facilitated by higher than ambient pressure.

Carbon disulfide has also proven useful in preparing various aryl and alkyl isothiocyanates by allowing it to react with a halomagnesium alkyl or arylamine (Gregnard reagent) forming, in situ a halomagnesium N-aryl(or alkyl)-N-halomagnesiodithiocarbonate. Thermal decomposition of the dithiocarbonate produces the desired aryl (or alkyl) isothiocyanate. See Sakai, et al, Bul. Chem. Soc. Japan, 48(10) 291 (1975).

While some of the processes of the above prior art yield acceptable quantities of the isothiocyanate product, they are generally quite inconvenient, utilizing reagents that are toxic (such as heavy metals and/or phosgeneous derivatives) or require difficult reaction conditions.

It has now been discovered that certain aryl isothiocyanates can be readily prepared in good yields by a simple thermal treatment. The isothiocyanates prepared by the process of the present invention are those of the formula

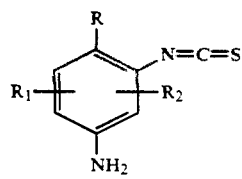

where R, $R_1$, and $R_2$ are the same or different and are hydrogen or $C_1$ to $C_6$ linear or branched alkyl.

In the above compounds, R is preferably $C_1$ to $C_6$ linear or branched alkyl different from $R_1$ and $R_2$. Most preferably $R_1$ and $R_2$ are the same and are $C_1$ to $C_6$ linear or branched alkyl. Particularly preferred are compounds of the above formula where R is methyl, and $R_1$ and $R_2$ are the same and are ethyl.

The process of this invention is typically carried out by using as reactants diamine compounds of the formula

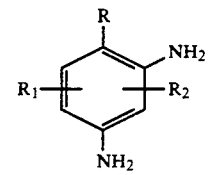

and thiourea. The compounds are mixed without a solvent and heated to about a range of 150° to 250° C. It should be noted that inert, organic solvents may optionally be used. However, reaction times are usually longer due to dilution effect on the reacting molecules. Preferably, the reaction is carried out at temperatures of from about 175° to 225° C. for 2 to 30 hours, most preferably about 185° to 215° C. for about 3 to about 7 hours.

The isothiocyanates formed are conveniently separated from the reaction mass by vacuum distillation. However, any other conventional method is also acceptable, e.g., extraction, recrystallization, etc.

The isothiocyanate resulting from this reaction is, surprisingly, a monoisocyanate. Thus, illustrative compounds prepared by the process of the present invention include:

3,5-dimethyl-4-aminotoluyl-2-isothiocyanate;
3,5-diethyl-4-aminotoluyl-2-isothiocyanate;
3,5-diisopropyl-4-aminotoluyl 2-isothiocyanate;
5,6-dimethyl-4-aminotoluyl-2-isothiocyanate;
5,6-diethyl-4-aminotoluyl-2-isothiocyanate;
5,6-dipropyl-4-aminotoluyl-2-isothiocyanate;
2,6-dimethyl-4-ethyl-3-isothiocyanatoaniline;
2,6-diethyl-4-ethyl-3-isothiocyanatoaniline;
2,6-triisopropyl-3-isothiocyanatoaniline;
2,6-dimethyl-4-propyl-3-isocyanatoaniline;
2,6-diethyl-4-propyl-3-isocyanatoaniline;
2,4,6-tripropyl-3-isocyanatoaniline;
3,5-dimethyl-6-aminotoluyl-2-isothiocyanate;
3,5-diethyl-6-aminotoluyl-2-isothiocyanate;
3,5-dipropyl-6-aminotoluyl-2-isothiocyanate;
3,5-dimethyl-2-aminotoluyl-4-isothiocyanate;
3,5-diethyl-2-aminotoluyl-4-isothiocyanate;
3,5-dipropyl-2-aminotoluyl-4-isothiocyanate;
2,4-dimethyl-6-ethyl-3-isothiocyanatoaniline;
2,4-diethyl-6-ethyl-3-isothiocyanatoaniline;
2,4-tripropyl-3-isothiocyanataniline;
2,4-dimethyl-6-isopropyl-3-isocyanatoaniline; and
2,4-diethyl-6-isopropyl-3-isocyanatoaniline.

After removal of the isothiocyanate by any of the conventional methods discussed above, a residue remains that produces a compound of the formula

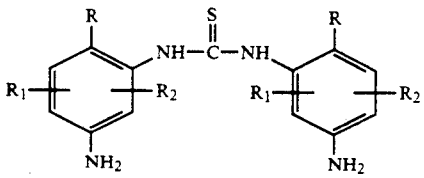

where R, $R_1$, and $R_2$ are as previously described.

These thioureas are high melting compounds that are sufficiently reactive to be used as heterogeneous chain extending agents in, for example, polyurethane, or polyimide, or polyamide preparations.

In the above thioureas, R, $R_1$, and $R_2$ are the same or different and are individually hydrogen or $C_1$ or $C_6$ linear or branched alkyl. Preferably, R is $C_1$ to $C_6$ linear or branched alkyl, different from $R_1$ and $R_2$. Most preferably, $R_1$ and $R_2$ are $C_1$ to $C_6$ linear or branched alkyl. Particularly preferred are R as methyl and $R_1$ and $R_2$ as ethyl.

Illustrative compounds of the present invention that are thioureas are as follows:

bis(3,5-dimethyl-4-aminotoluyl-2)-thiourea;
bis(3,5-diethyl-4-aminotoluyl-2)-thiourea;
bis(3,5-dipropyl-4-aminotoluyl-2)-thiourea;
bis(3,5-dimethyl-2-aminotoluyl-4)-thiourea;
bis(3,5-diethyl-2-aminotoluyl-4)-thiourea;
bis(3,5-diisopropyl-2-aminotoluyl-4),-thiourea;
N-(3,5-dimethyl-4-aminotoluyl-2)-N'-(3,5-dimethyl-2-aminotoluyl-4)-thiourea;
N-(3,5-diethyl-4-aminotoluyl-2)-N'-(3,5-diethyl-2-aminotoluyl-4)-thiourea; and
N-(3,5-diisopropyl-4-aminotoluyl-2)-N'-(3,5-diisopropyl-2-aminotoluyl-4)-thiourea.

The process and compounds of the invention are illustrative by the following examples which are intended to not limit the scope of the invention in any way.

EXAMPLES

Example 1

In a 500 ml flask equipped with thermocouple thermometer, magnetic stirrer and condenser, add 92.5 parts of DETDA (80% 3,5-diethyl 2,4-toluenediamine and 20% 3,5-diethyl 2,6-toluenediamine) and 20 parts of thiourea. The reaction mixture was flushed with nitrogen and the flask contents were heated to 170° C. (pot temperature) for 6 hours. Early in the reaction, the product was bubbly. A sparge tube was added to the reaction mixture to remove evolved ammonia. Then the product was dumped out while still hot onto a cooled metal sheet where the product mixture solidified to a glass and was broken up to give 75 parts of a yellow powder.

The yellow solid was distilled to separate the products. In a short path distillation apparatus, at 163° C. bath temperature and 0.4 torr a mobile liquid was collected (46.8 parts). Analysis showed this mixture to be 64% DETDA (both the 2,4- and 2,6-isomers) and 36% of amino diethyl toluyl isothiocyanates. There are three mono isothiocyanates (50%, 33% and 17% yield), two from 2,4-diamine and one from the 2,6-diamine. All three are seen in a gas chromatographic analysis.

The residue remaining behind after distillation was 24.1 parts. Analysis for molecular weight by VPO (vapor phase osmometry) showed a mol wt. of 413 for the solid residue. The calculated value for the di-substituted thiourea is 398.

Solubility tests on this solid thiourea was as follows:

| Solvent | Solubility |
| --- | --- |
| Heptane | insoluble |
| Ether | insoluble |
| Toluene | insoluble |
| Ethanol | soluble |
| Acetone | soluble |
| Pyridine | soluble |
| Dimethylsulfoxide | soluble |
| N-methylpyrrolidone | insoluble |
| Dioxane | soluble |

EXAMPLE 2

In a similar run to Example 1, 176 parts of DETDA (diethyl toluene diamine) and 38 parts of thiourea were heated for 26 hours at 185° C. After workup in the same way as shown in Example 1, a yellow solid was obtained. Workup by distillation gave:

24% DETDA (recovered)
10% Mono isothiocyanates of DETDA (same three isomers)
66% Solid di-substituted thioureas

Example 3

Using less thiourea gave less of both products.

When reacting 72 parts of DETDA and 7 parts of thiourea and heating the mixture at 169° C. for 5 hours, with subsequent workup to the yellow solid and distillation afforded the following:
67% Recovered DETDA
7% Mono isothiocyanates of DETDA (three isomers)
28% Di-substituted thioureas

I claim:

1. A process for the preparation of N,N'-diarylthioureas and arylisothiocyanates comprising treating a compound of the formula:

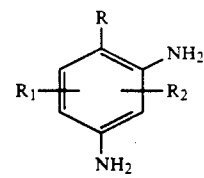

where R, $R_1$ and $R_2$ are the same or different and are hydrogen or $C_1$ to $C_6$ linear or branched alkyl with thiourea at a temperature of from about 150° C. to about 250° C. and separating said N,N'-diarylthiourea and arylisothiocyanate from the mixture produced from said treating.

2. The process according to claim 1 wherein R is $C_1$ to $C_6$ linear or branched alkyl.

3. The process according to claim 2 where $R_1$ to $R_2$ are the same and are $C_1$ to $C_6$ linear or branched alkyl.

4. The process according to claim 3 where R is methyl and $R_1$ and $R_2$ are the same and are ethyl.

5. The process according to claim 1 where a compound of the formula,

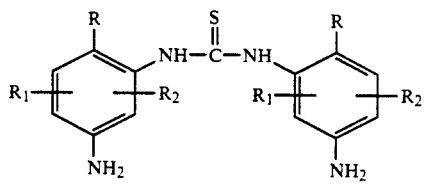
where R, $R_1$, and $R_2$ are as previously defined, is separated from the mixture produced from said treating.
6. The process according to claim 5 where in R is $C_1$ to $C_6$ linear or branched alkyl.
7. The process according to claim 6 where $R_1$ and $R_2$ are the same and are $C_1$ to $C_6$ linear or branched alkyl.
8. The process according to claim 7 where R is methyl and $R_1$ and $R_2$ are ethyl.
* * * * *